United States Patent
Fontana, Jr. et al.

(10) Patent No.: US 7,806,585 B2
(45) Date of Patent: Oct. 5, 2010

(54) APPARATUS, METHOD, AND SYSTEM FOR MEASURING WATER ACTIVITY AND WEIGHT

(75) Inventors: Anthony J. Fontana, Jr., Pullman, WA (US); Gaylon S. Campbell, Pullman, WA (US); Colin S. Campbell, Pullman, WA (US); Benjamin J. Walden, Moscow, ID (US); Derek L. Holmes, Pullman, WA (US)

(73) Assignee: Decagon Devices, Inc., Pullman, WA (US)

( * ) Notice: Subject to any disclaimer, the term of this patent is extended or adjusted under 35 U.S.C. 154(b) by 321 days.

(21) Appl. No.: 11/767,460

(22) Filed: Jun. 22, 2007

(65) Prior Publication Data

US 2008/0317089 A1    Dec. 25, 2008

(51) Int. Cl.
*G01N 25/02*    (2006.01)
(52) U.S. Cl. .......................................... 374/27
(58) Field of Classification Search ............ 374/27; 324/636, 700; 73/73
See application file for complete search history.

(56) References Cited

U.S. PATENT DOCUMENTS

| | | | |
|---|---|---|---|
| 2,758,502 | A | 8/1956 | Scott et al. |
| 6,063,332 | A | 11/1962 | Fajans |
| 3,142,986 | A | 8/1964 | Wood et al. |
| 3,350,978 | A | 11/1967 | Alers |
| 3,643,402 | A | 2/1972 | Wireman |
| 3,652,844 | A | 3/1972 | Scott, Jr. |
| 3,733,133 | A | 5/1973 | Chapman |
| 3,771,548 | A | 11/1973 | Rauchwerger |
| 3,965,416 | A | 6/1976 | Friedman |
| 3,968,428 | A | 7/1976 | Numoto |
| 4,025,193 | A | 5/1977 | Pond et al. |
| 4,052,666 | A | 10/1977 | Fletcher et al. |
| 4,154,507 | A | 5/1979 | Barr |
| 4,177,434 | A | 12/1979 | Ida |

(Continued)

FOREIGN PATENT DOCUMENTS

AT          403213          10/1997

(Continued)

OTHER PUBLICATIONS

Galon S. Cambell and Russell Y. Anderson, "Evaluation of Simple Transmission Line Oscillators for Soil Moisture Measurement", Computers and Electronics in Agriculture p. 31.

*Primary Examiner*—Andre J Allen
(74) *Attorney, Agent, or Firm*—Holland & Hart

(57) ABSTRACT

An apparatus configured to determine water activity and weight of a sample. The apparatus may comprise a chamber configured to at least partially enclose a sample. The apparatus may also comprise a sensor configured to measure water activity of a sample in the chamber. Additionally, the apparatus may comprise a moisture content adjustment device connected to the chamber and configured to change moisture content in the chamber. An isotherm generation module is also disclosed. The isotherm generation module may be configured to receive water activity measurements from a sensor device and weight measurements from a weighing device, the isotherm generation module being configured to generate an isotherm for a sample based on the water activity measurements and the weight measurements.

40 Claims, 7 Drawing Sheets

U.S. PATENT DOCUMENTS

| | | | |
|---|---|---|---|
| 4,277,170 A | 7/1981 | Miles |
| 4,310,758 A | 1/1982 | Peterson |
| 4,341,112 A | 7/1982 | Mackay et al. |
| 4,364,183 A | 12/1982 | Rhodes |
| 4,387,297 A | 6/1983 | Swartz et al. |
| 4,389,900 A | 6/1983 | Gutierrez |
| 4,409,470 A | 10/1983 | Shepard et al. |
| 4,556,278 A | 12/1985 | Schell |
| 4,568,825 A | 2/1986 | Wurster |
| 4,572,662 A | 2/1986 | Silverman |
| 4,579,462 A | 4/1986 | Rall et al. |
| 4,646,000 A | 2/1987 | Wills |
| 4,647,761 A | 3/1987 | Cojan et al. |
| 4,752,689 A | 6/1988 | Satake |
| 4,801,804 A | 1/1989 | Rosenthal |
| 4,850,687 A | 7/1989 | Reis et al. |
| 4,866,464 A | 9/1989 | Straayer |
| 4,871,904 A | 10/1989 | Metlitsky et al. |
| 5,100,229 A | 3/1992 | Lundberg et al. |
| 5,136,249 A | 8/1992 | White et al. |
| 5,137,354 A | 8/1992 | DeVos et al. |
| 5,146,463 A | 9/1992 | Rando |
| 5,148,008 A | 9/1992 | Takenaka |
| 5,148,125 A | 9/1992 | Woodhead |
| 5,212,453 A | 5/1993 | Koehler et al. |
| 5,214,531 A | 5/1993 | Torii et al. |
| 5,258,822 A | 11/1993 | Nakamura et al. |
| 5,272,353 A | 12/1993 | Barkan et al. |
| 5,298,729 A | 3/1994 | Wike, Jr. |
| 5,302,026 A | 4/1994 | Phillips |
| 5,321,259 A | 6/1994 | Morgan |
| 5,376,888 A | 12/1994 | Hook |
| 5,402,075 A | 3/1995 | Lu et al. |
| 5,424,649 A | 6/1995 | Gluck et al. |
| 5,445,178 A | 8/1995 | Feuer |
| 5,459,403 A | 10/1995 | Kohler et al. |
| 5,507,175 A | 4/1996 | Cooper |
| 5,546,217 A | 8/1996 | Greenway |
| 5,816,704 A | 10/1998 | Cambell et al. |
| 5,859,536 A | 1/1999 | Stockton |
| 5,969,620 A | 10/1999 | Okulov |
| 6,060,889 A | 5/2000 | Hocker |
| 6,107,809 A | 8/2000 | Moshe et al. |
| 6,204,670 B1 | 3/2001 | Joshi |
| 2003/0169058 A1* | 9/2003 | Pierre et al. .................. 324/700 |
| 2007/0018657 A1* | 1/2007 | Nagata et al. ................ 324/636 |
| 2007/0181147 A1* | 8/2007 | Satake ......................... 134/1.2 |
| 2008/0105041 A1* | 5/2008 | Dziki ............................ 73/73 |
| 2009/0188984 A1* | 7/2009 | Al-Qassem ................ 236/44 A |

FOREIGN PATENT DOCUMENTS

| | | |
|---|---|---|
| DE | 2634274 | 2/1978 |
| FR | 1128606 | 2/1957 |
| RU | 1659818 | 6/1991 |

* cited by examiner

APPARATUS, METHOD, AND SYSTEM FOR MEASURING WATER ACTIVITY AND WEIGHT

BACKGROUND

The relationship between water activity and moisture content at a given temperature may be referred to as a moisture sorption isotherm. Moisture sorption isotherms show the relationship between water activity and moisture content for a particular sample at a given temperature. For example, a graph of a moisture sorption isotherm may illustrate a relationship between water activity and moisture content by showing moisture content on a y-axis of the graph and water activity on an x-axis of the graph. A moisture sorption isotherm may be used to estimate shelf-life of a food product. Moisture sorption isotherms may be particularly useful in developing new food products, in characterizing ingredients, in determining packaging requirements for food products, and in various areas of research and development requiring a knowledge of the relationship between water activity and moisture content for a particular product at a given temperature.

A traditional method for obtaining a moisture sorption isotherm may be to place a food sample, either dried (absorption), hydrated (desorption), or native (working), into a controlled humidity chamber at constant temperature. The next step may be measuring the weight of the sample until the weight reaches equilibrium. This process may need to be repeated numerous times to acquire enough data points to generate a useful isotherm. The entire process may take up to three weeks. The large amount of time and labor that may be required to obtain an isotherm may be prohibitive for obtaining isotherms in various instances.

SUMMARY

In certain embodiments, a measurement apparatus may comprise a chamber. The measurement apparatus may also comprise a sensor configured to measure water activity of a sample in the chamber. The measurement apparatus may also comprise a moisture content adjustment device connected to the chamber and configured to change moisture content in the chamber. In at least one embodiment, a measurement apparatus may comprise a weighing device coupled to the chamber.

In at least one embodiment, a measurement apparatus may comprise an isotherm generation module configured to receive measurements from the sensor device and the weighing device, the isotherm generation module being configured to generate an isotherm for a sample positioned in the chamber. In at least an additional embodiment, an isotherm generation module may generate the isotherm by compiling a plurality of data points, each data point in the plurality of data points representing a measurement received from the sensor device and a measurement received from the weighing device.

According to various embodiments, the weighing device may comprise a scale coupled to the chamber. According to at least an additional embodiment, the weighing device may comprise a balance coupled to the chamber. In at least another embodiment, the balance may comprise a magnetic force balance. In certain embodiments, at least a portion of the weighing device may be positioned within the chamber.

According to some embodiments, a fan may be positioned within the chamber. In at least one embodiment, a heating element may be coupled to the chamber. In at least an additional embodiment, a cooling element may be coupled to the chamber. In certain embodiments, a heating element may be configured to heat gas supplied by the moisture content adjustment device. According to some embodiments, a cooling element may be configured to cool gas supplied by the moisture content adjustment device.

In at least one embodiment, a valve may be configured to control passage of air between the chamber and a region external to the chamber. In some embodiments, the moisture content adjustment device may comprise a humidification device. In certain embodiments, the moisture content adjustment device may comprise a desiccation device. In various embodiments, the moisture content adjustment device may comprise a gas supply. According to certain embodiments, the moisture content adjustment device may comprise a pump configured to supply gas from the gas supply to the chamber.

In various embodiments, the moisture content adjustment device may comprise a humidification device. In certain embodiments, the moisture content adjustment device may comprise a desiccation device. In at least one embodiment, the moisture content adjustment device may comprise a valve configured to deliver gas from the pump to the humidification device. In at least an additional embodiment, the moisture content adjustment device may comprise a valve configured to deliver gas from the pump to the desiccation device.

According to certain embodiments, the sensor may comprise a water activity sensor. In at least one embodiment, the sensor may comprise a humidity sensor. In at least an additional embodiment, the sensor may comprise a dew point sensor. In at least an additional embodiment, the sensor may comprise a freezing point sensor. According to at least one embodiment, the sensor may comprise an optical sensor. According to various embodiments, the sensor may comprise a sensor adapted to detect spectral data. The sensor may comprise a chilled-mirror dew point sensor positioned within the chamber.

A method may comprise determining a first water activity measurement of a sample in a chamber during a first time period. The method may also comprise determining a first weight of the sample in the chamber during the first time period. The method may further comprise changing moisture content in the chamber during a second time period, the second time period being after the first time period. In addition, the method may comprise determining a second water activity measurement of the sample during a third time period, the third time period being after the second time period. The method may further comprise determining a second weight of the sample during the third time period.

In at least one embodiment, a method may comprise changing the moisture content in the chamber during a fourth time period, the fourth time period being after the third time period. The method may also comprise determining a third water activity measurement of the sample during a fifth time period, the third time period being after the fourth time period. In addition, the method may comprise determining a third weight of the sample during the fifth time period.

In at least an additional embodiment, the method may comprise preventing a change in moisture content in the chamber during the determination of the first water activity measurement of the sample in the chamber during the first time period. The method may comprise preventing a change in moisture content in the chamber during the determination of the first weight of the sample in the chamber during the first time period.

In certain embodiments, the method may comprise heating the chamber to within a specified temperature range. In addition, the method may comprise cooling the chamber to within a specified temperature range. The method may also comprise circulating air within the chamber during determination of the first water activity measurement of the sample in the chamber during the first time period. The method may additionally comprise circulating air within the chamber during determination of the second water activity measurement of the sample in the chamber during the second time period. The method may further comprise determining the first water activity measurement of the sample at least substantially simultaneously with determining the first weight of the sample. Determining the first water activity measurement may be performed while the sample is positioned on a balance in the chamber. Additionally, changing the moisture content in the chamber may comprise adding moisture to the chamber. In certain embodiments, changing the moisture content in the chamber may comprise removing moisture from the chamber. In addition, changing the moisture content in the chamber may comprise supplying a gas and vapor mixture to the chamber.

A computer-implemented method for generating an isotherm may comprise determining a first water activity measurement of a sample during a first measuring period, the first water activity measurement being determined with a water activity sensor. The method may also comprise determining a first weight of the sample during the first measuring period, the sample being positioned in a chamber during the first measuring period. In addition, the method may comprise determining a first isotherm data point based on the first water activity measurement of the sample and the first weight of the sample.

According to certain embodiments, the method may comprise changing moisture content in the chamber after the first measuring period and before a second measuring period. Changing the moisture content in the chamber may comprise adding moisture to the chamber. Changing the moisture content in the chamber may also comprise removing moisture from the chamber. The method may additionally comprise adding moisture content to the chamber after the first measuring period and before a second measuring period. Also, the method may comprise removing moisture content from the chamber after the second measuring period and before a third measuring period. Determining the first water activity measurement of the sample may be performed at least substantially simultaneously with determining the first weight of the sample. Determining the first water activity measurement may be performed while the sample is positioned on a balance in the chamber. The method may additionally comprise determining a hydration curve of an isotherm based on a plurality of water activity measurements of the sample and a plurality of weights of the sample. The plurality of water activity measurements may comprise the first water activity measurement. In addition, the plurality of weights may comprise the first weight. Each water activity measurement in the plurality of water activity measurements may be determined while the sample is in the chamber. Further, each weight in the plurality of weights may be determined while the sample is in the chamber.

In various embodiments, an isotherm generator may comprise a chamber. In at least an additional embodiment, a sensor may be configured to measure water activity of a sample in the chamber. In certain embodiments, a moisture content adjustment device may be connected to the chamber and configured to change moisture content in the chamber. According to at least another embodiment, a weighing device may be coupled to the chamber and configured to weigh the sample in the chamber. According to certain embodiments, an isotherm generation module may be configured to receive water activity measurements from the sensor device and weight measurements from the weighing device, the isotherm generation module being configured to generate an isotherm for the sample, the isotherm being based on the water activity measurements and the weight measurements. The weighing device may comprise a magnetic force balance. The sensor device may comprise a chilled-mirror dew point sensor. The sample may be a food product, a soil sample, a pharmaceutical product, a consumer product, or any other suitable type of sample.

According to various embodiments, the isotherm generator may comprise a gas supply. The isotherm generator may additionally comprise a pump configured to pump gas from the gas supply to the chamber. The moisture content adjustment device may comprise a humidification device. The moisture content adjustment device may also comprise a desiccation device. The moisture content adjustment device may further comprise a valve configured to deliver gas from the pump to the humidification device. The moisture content adjustment device may also comprise a valve configured to deliver gas from the pump to the humidification device to the desiccation device.

According to certain embodiments, the isotherm generator may comprise a heating device. The isotherm generator may also comprise a cooling device, the heating and cooling device being configured to control a temperature of the chamber and sample.

BRIEF DESCRIPTION OF THE DRAWINGS

The accompanying drawings illustrate a number of exemplary embodiments and are a part of the specification. Together with the following description, these drawings demonstrate and explain various principles of the instant disclosure.

DETAILED DESCRIPTION

Figure 1:
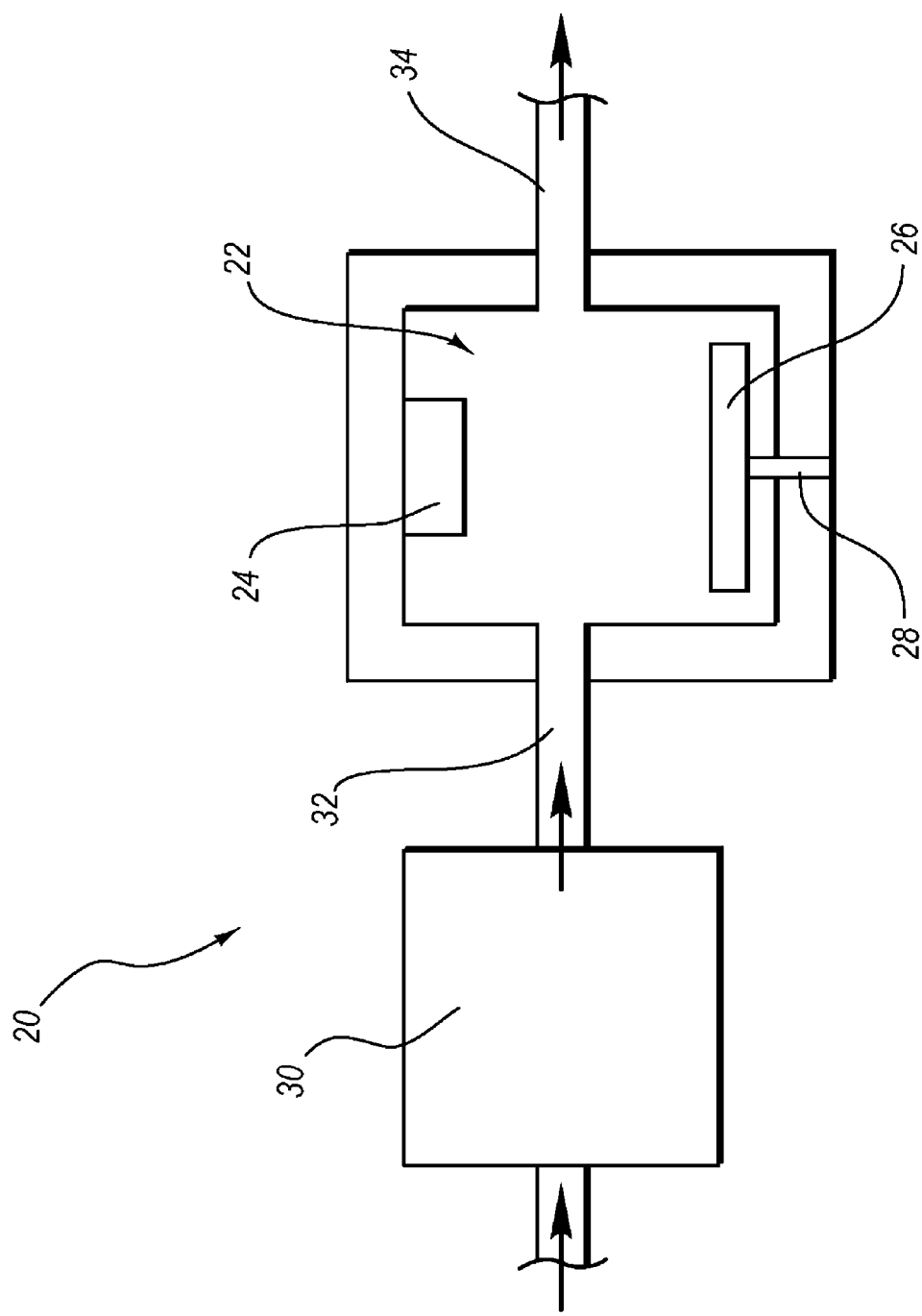
FIG. 1 is an illustration of an exemplary measuring apparatus for measuring water activity and weight of a sample according to certain embodiments.

Throughout the drawings, identical reference characters and descriptions indicate similar, but not necessarily identical, elements. While embodiments of the instant disclosure are susceptible to various modifications and alternative forms, specific embodiments have been shown by way of example in the drawings and will be described in detail herein. However, one of skill in the art will understand that embodiments of the instant disclosure are not intended to be limited to the particular forms disclosed herein. Rather, the instant disclosure covers all modifications, equivalents, and alternatives falling within the scope of embodiments defined by the appended claims.

The instant disclosure presents various examples of measuring apparatus for measuring water activity and weight of a sample. According to some embodiments, the measuring devices disclosed herein may efficiently obtain measurements of water activity and weight of a sample, enabling rapid generation of a moisture sorption isotherm. The measuring apparatus may also obtain a large number of measurements of water activity of a sample and weight of a sample, enabling rapid creation of a detailed isotherm. For example, in at least one exemplary embodiment, the measuring device may generate complete isotherms having more than 100 data-points within a time period of approximately twenty-four hours or less. The measuring device may also generate more or less than 100 data points. Additionally, in some embodiments, the measuring apparatus may be easily operated because water activity and weight measurements for the isotherm may be obtained from a single sample positioned inside the chamber of the measuring apparatus.

FIG. 1 shows a measuring apparatus 20 which may measure water activity and weight of a sample. According to various embodiments, the measuring apparatus 20 may be used to obtain multiple measurements of water activity and weight of a sample to generate a moisture sorption isotherm.

Water activity measurements may serve several useful purposes. Water activity may be measured in plants, soils, and foods, as well as other product samples. Most commonly, water activity may be measured with respect to food products. Water activity or water potential may be measured in food products to determine or predict food stability with respect to physical properties, rates of deteriorative reactions, and/or microbial growth. Water activity may be a primary factor that determines shelf life of food products. Several other factors, such as temperature and pH, can influence the growth of organisms in food products. Among the factors that affect organism growth in food products, water activity may be the most important.

Water activity may be indicative of the energy required to remove a small amount of water from the sample. Water activity may be represented as a ratio between the vapor pressure of the sample when the sample is in balance with the surrounding air media, and the vapor pressure of distilled water under identical conditions. A water activity measurement of 0.80 may indicate that the vapor pressure of the sample is eighty percent of the vapor pressure of pure water at the same conditions. Water activity may be typically measured by equilibrating a small sample of a product in a sealed container and determining the relative humidity of a headspace. If the sample and the headspace are in thermal and vapor equilibrium, the humidity of the headspace may be equal to the water activity of the sample. Knowledge of water activity may be critical in determining the safety of a variety of shelf-stable foods. If a product has a water activity less than or equal to approximately 0.85, the product may not support the growth of pathogenic bacteria, regardless of the water content of the product.

Measuring apparatus 20 may include a chamber 22. A sensor 24 may be configured to measure water activity within chamber 22. Sensor 24 may be positioned within chamber 22. In some embodiments, sensor 24 may be located external to chamber 22 in a position that allows sensor 24 to measure water activity within the chamber 22. Additionally, a moisture content adjustment device 30 may be connected to chamber 22 by chamber inlet 32. According to at least one embodiment, chamber 22 may also include a weighing device 26. In at least one embodiment, chamber 22 may have a chamber outlet 34.

As illustrated in FIG. 1, chamber 22 may comprise a space which may be at least partially enclosed. Chamber 22 may be opened to receive a sample within chamber 22. Chamber 22 may be formed of any suitable material. As embodiments discussed herein illustrate, chamber 22 may be various shapes, sizes, and configurations. In at least one embodiment, chamber 22 may be formed to a shape, size, and configuration suitable for receiving and at least partially enclosing a food sample. According to some embodiments, the sample may be a soil sample, a pharmaceutical product, a consumer product, or any other suitable type of sample. In an exemplary embodiment, chamber inlet stream 32 may introduce a vapor composition, a gas composition, and/or any other suitable material into chamber 22. Chamber 22 may also include a chamber outlet 34, which may allow any vapors introduced or produced in chamber 22 to be evacuated from chamber 22.

Moisture content adjustment device 30 may include a device configured to increase or decrease the overall moisture content present in chamber 22. For example, moisture content adjustment device 30 may include a device which produces a humidified gas, a device which increases the humidity of chamber 22 through evaporation, a device which produces a dry gas, and/or any other suitable device for adjusting moisture content in chamber 22.

A weighing device 26 may be located at least partially within chamber 22, as shown in FIG. 1. Alternatively, weighing device 26 may be located external to chamber 22. In an example where weighing device 26 is external to chamber 22, weighing device may be coupled to chamber 22 in such a manner that the weight of the chamber contents may be determined. Weighing device 26 may include scales, balances, or any other device capable of determining a sample weight. In certain embodiments, a weighing device 26 may include magnetic force balance.

Sensor 24, which may measure water activity within chamber 22, may be positioned within chamber 22, or alternatively, sensor 24 may be located external to chamber 22. Sensor 24 may include a water activity sensor, a humidity sensor, a dew point sensor, an optical sensor, a sensor adapted to detect spectral data, or any other sensor suitable for determining water activity. In particular, sensor 24 may be a chilled mirror dew point sensor, a hair hygrometer, a polymer hygrometer, an electric hygrometer, or a spectral detector.

Figure 2:
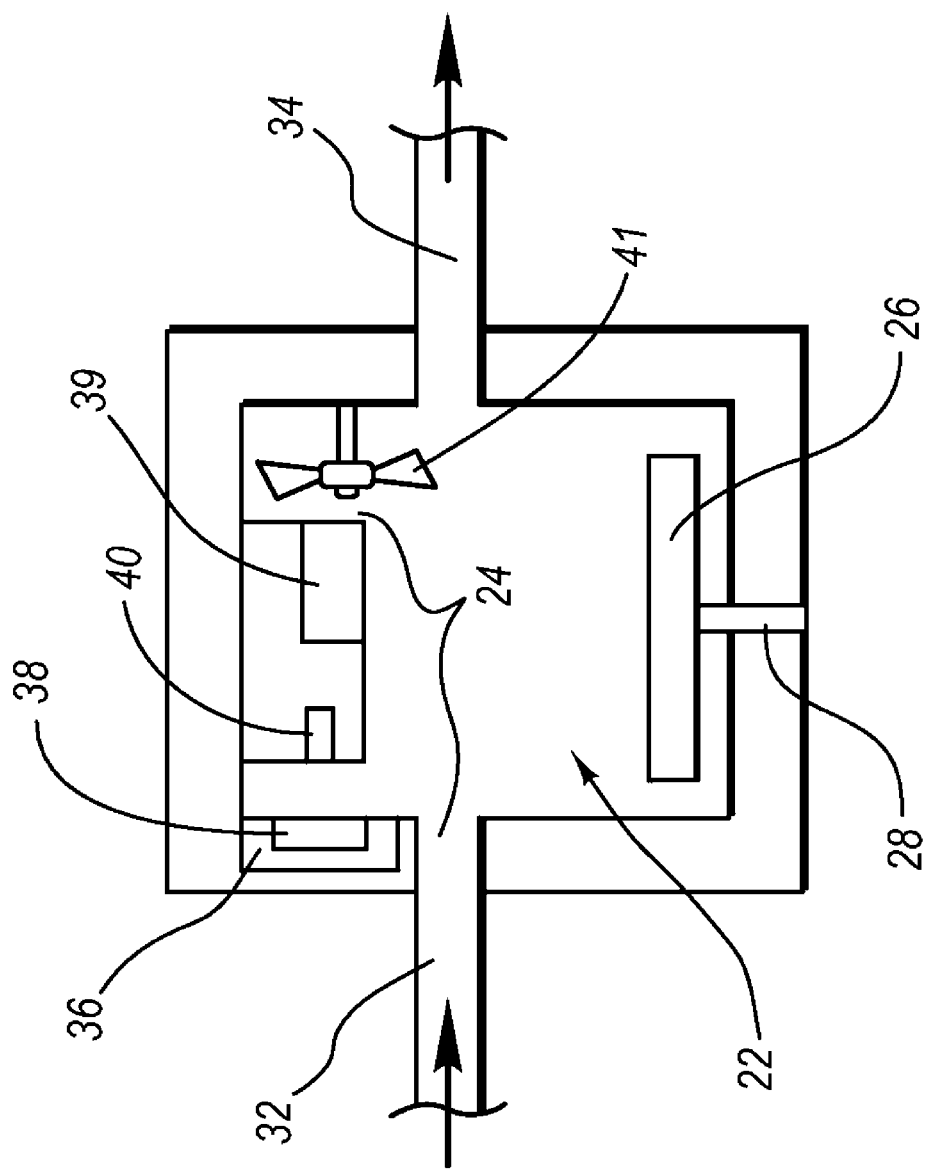
FIG. 2 is an illustration of an exemplary chamber for measuring a sample according to certain embodiments.

FIG. 2 illustrates at least one embodiment of chamber 22. Chamber 22 may include a sensor 24 which may measure water activity of a sample in chamber 22. As illustrated in FIG. 2, sensor 24 may be positioned inside chamber 22. In an exemplary embodiment, sensor 24 may be a chilled mirror dew point sensor which includes a thermo-electric cooler 36, a mirror 38 attached to the thermo-electric cooler 38, and an optical sensor 40. Thermo-electric cooler 36 may be a so-called Peltier cooler or any cooler suitable for use in sensor 24. A thermo-electric cooler 36 may cool mirror 38 until dew, or condensation, forms on the surface of mirror 38, and may subsequently heat mirror 38 until the dew formed on the surface of mirror 38 disappears. The optical sensor 40 may be positioned to detect a change in condensation on the mirror. More particularly, the optical sensor 40 may detect a formation or dissipation of dew on the surface of mirror 38. A temperature sensor may be coupled to the mirror to detect the temperature of the mirror as the dew is formed or dissipated. A precise dew point temperature may be obtained by forming and dissipating dew from the surface of mirror 38 and detecting the temperature at which the dew is initially formed and initially dissipated. An accurate water activity measure may be obtained from the dew point temperature measured by sensor 24. In some cases the water activity obtained by a chilled mirror dew point sensor may be accurate to ±0.003 $a_w$ (water activity). Sensor 24 may also include a temperature sensor 39 for measuring a temperature of the sample. Temperature sensor 39 may be an infrared sensor, a thermopile, or any other suitable type of temperature sensor.

A circulating device 41 may additionally be positioned within chamber 22. The circulating device 41 may be a fan, pump, or any suitable device for moving or circulating air within chamber 22. Circulating air within chamber 22 may decrease the time required to reach an equilibrium in chamber 22 suitable for obtaining a water activity measurement using sensor 24. Circulating air within chamber 22 may also increase the accuracy of a measurement obtained by the sensor 24.

Figure 3:
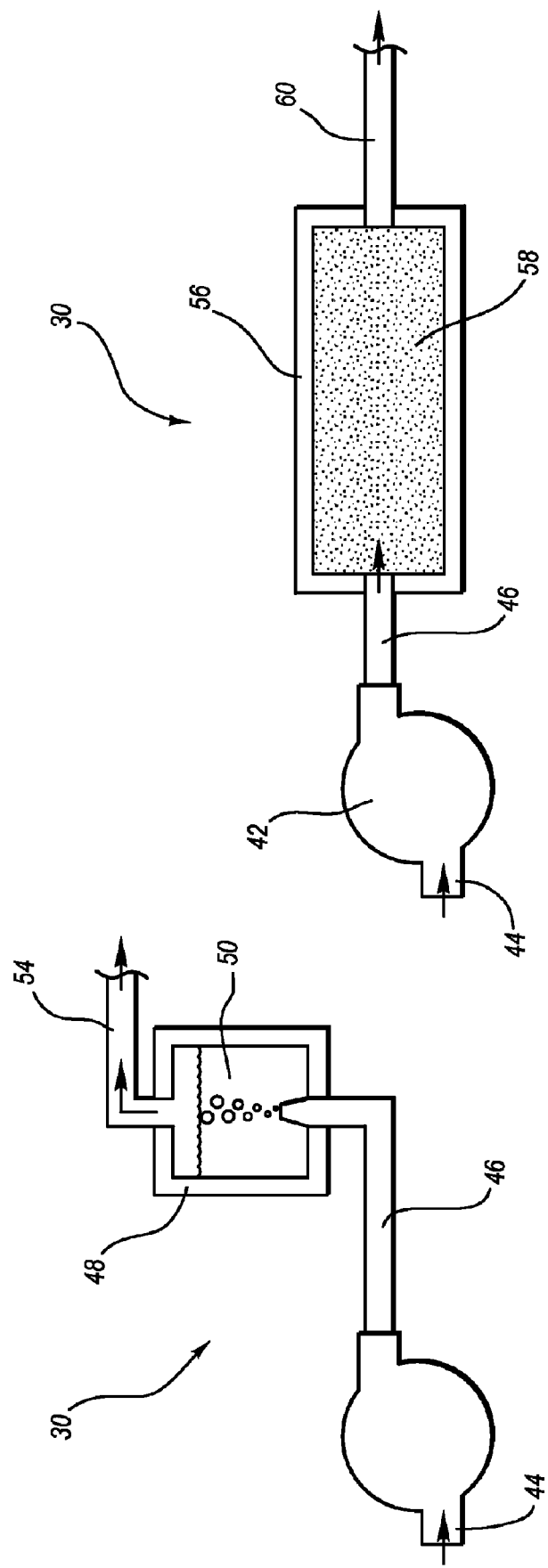
FIG. 3A is an illustration of an exemplary moisture content adjustment device 30 according to certain embodiments.
FIG. 3B is an illustration of an exemplary moisture content adjustment device 30 according to certain embodiments.

FIGS. 3A and 3B illustrate exemplary embodiments of moisture content adjustment device 30. In FIG. 3A, moisture content adjustment device 30 may include a pump 42, a pump inlet 44, a pump outlet 46, a humidification device 48, and a humidification device outlet 54. Pump 42 may be a positive displacement pump, a diaphragm pump, or any type of pump suitable for moving a gas mixture. Humidification device 48 may include a water bath 50 that contains water. In at least one embodiment, humidification device 48 may be connected to an end of pump outlet 46 that is opposite an end connected to pump 42. Pump outlet 46 may be connected to a lower portion of water bath 50 in humidification device 48. Humidification device 48 may produce a humidified gas mixture by receiving a gas mixture from pump outlet 46 and causing the gas mixture to increase in humidity as it passes from pump outlet 46 through the water in water bath 50. Humidification device outlet 54 may be connected to humidification device 48 to output the humidified gas mixture from the humidification device 48.

In at least an additional embodiment shown in FIG. 3B, moisture content adjustment device 30 may include a pump 42, a pump inlet 44, a pump outlet 46, a desiccation device 56, and a desiccation device outlet 60. Pump 42 may be a positive displacement pump, a diaphragm pump, or any type of pump suitable for moving a gas mixture. Desiccation device 56 may be a gas drying unit containing a desiccant material or any drying device capable of removing moisture from a gas mixture. Desiccation device 56 may contain a desiccant material 58 having a visual indicator that may change color when the desiccant material 58 declines in desiccation activity. Desiccation device 56 may produce a dry gas mixture by receiving a gas mixture from pump outlet 46 and causing the gas mixture to decrease in humidity as it passes from pump outlet 46 through desiccant material 58 in desiccation device 56. Desiccation device outlet 60 may be connected to desiccation device 56 to output the dry gas mixture from the desiccation device 56.

Figure 4:
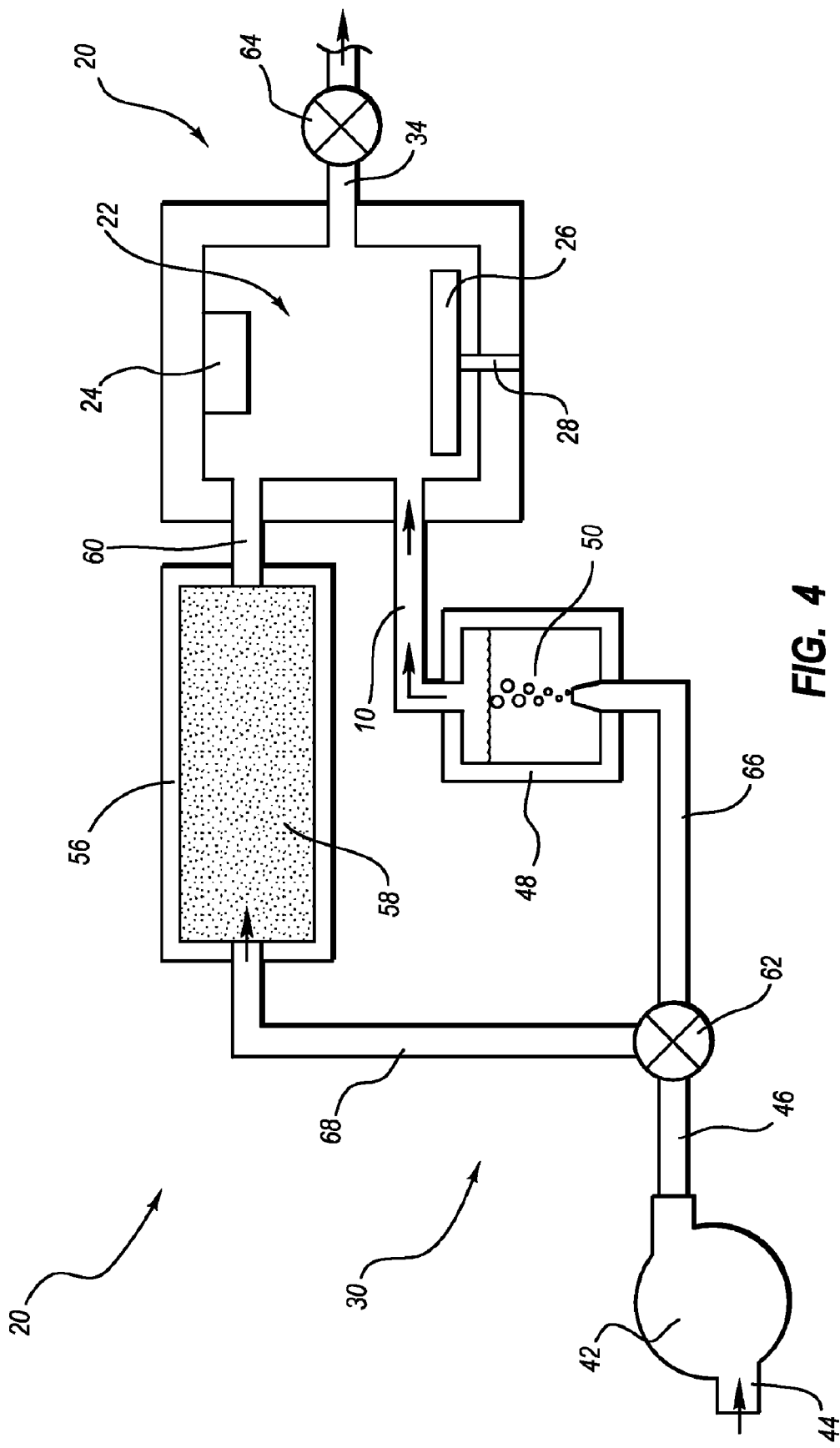
FIG. 4 is an illustration of an exemplary measuring apparatus for measuring water activity and weight of a sample according to certain embodiments.

FIG. 4 shows an exemplary embodiment of moisture content adjustment device 30 which includes a humidification device and a desiccation device. Moisture content adjustment device 30 may include a pump 42, a pump inlet 44, a pump outlet 46, a moisture content adjustment valve 62, a humidification device 48, a humidification device inlet 66, a humidification device outlet 54, a desiccation device 56, a desiccation device inlet 68, and a desiccation device outlet 60. As described above with reference to the exemplary embodiment illustrated in FIG. 3A, humidification device 48 may include a water bath 50 containing water. Additionally, as described above with reference to the exemplary embodiment illustrated in FIG. 3B, desiccation device 56 may include a desiccant material 58. In at least one embodiment, as illustrated in FIG. 4, moisture content adjustment valve 62 may be a valve or any device suitable for controlling a flow of gas from pump 42 to humidification device 48 and/or desiccation device 56. Moisture content adjustment valve 62 may allow delivery of humidified gas and dry gas to sample chamber 22.

In at least one embodiment, chamber outlet 34 may be connected to a chamber outlet valve 64, as illustrated in FIG. 4. Chamber outlet valve 64 may be a valve or any device suitable for controlling a flow of gas between chamber 22 and a region external to chamber 22. The chamber outlet valve 64 may allow or restrict a flow of gas from chamber 22. In an exemplary embodiment, the chamber outlet valve 64 may prevent exchange of gas between chamber 22 and a region external to chamber 22 when a water activity measurement is being obtained by sensor 24 in chamber 22. Alternatively, the chamber outlet valve 64 may allow exchange of gas between chamber 22 and a region external to chamber 22 when a moisture content in chamber 22 is being adjusted.

Figure 5:
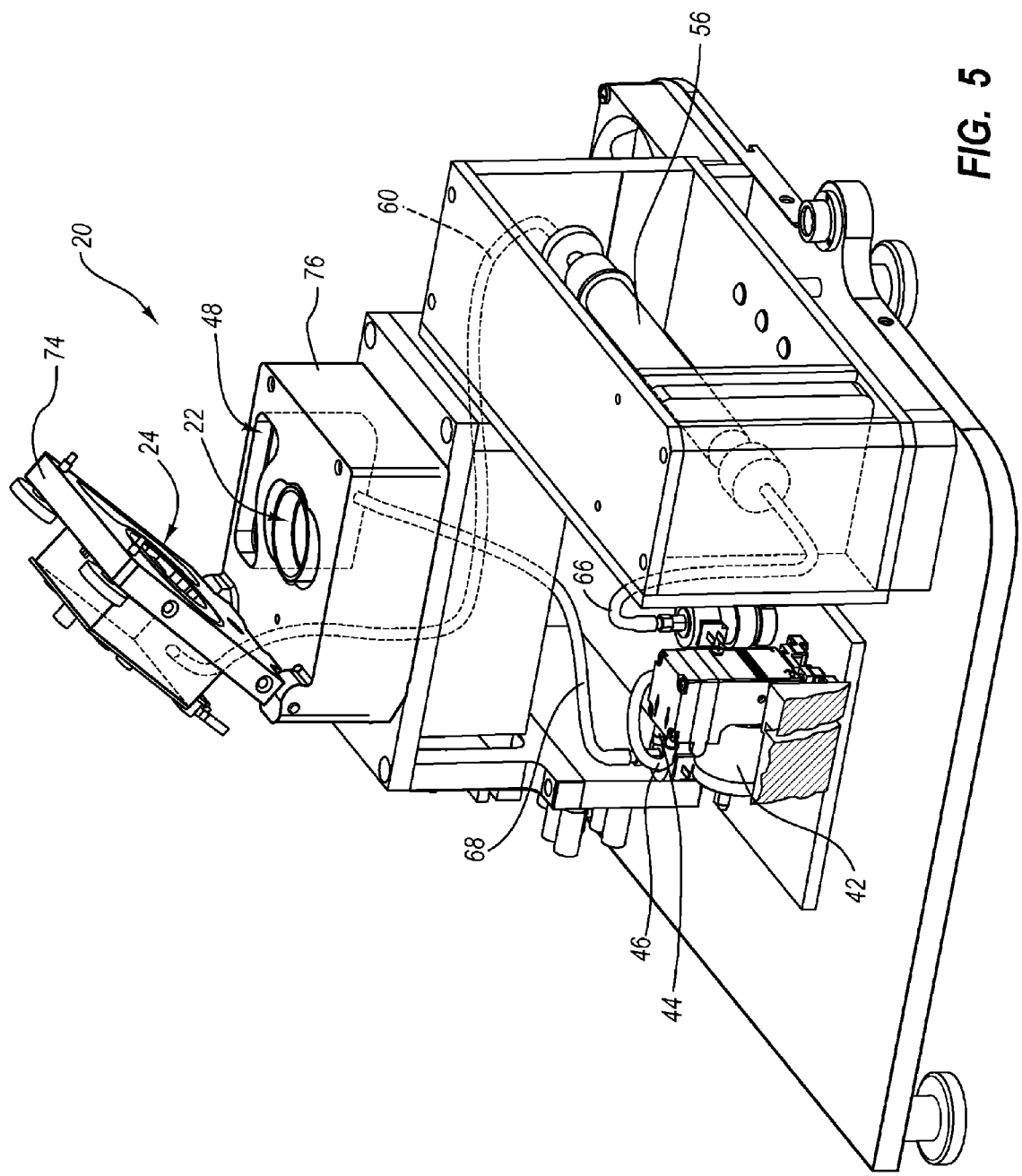
FIG. 5 is a perspective view of an exemplary measuring apparatus for measuring water activity and weight of a sample according to certain embodiments.
Figure 6:
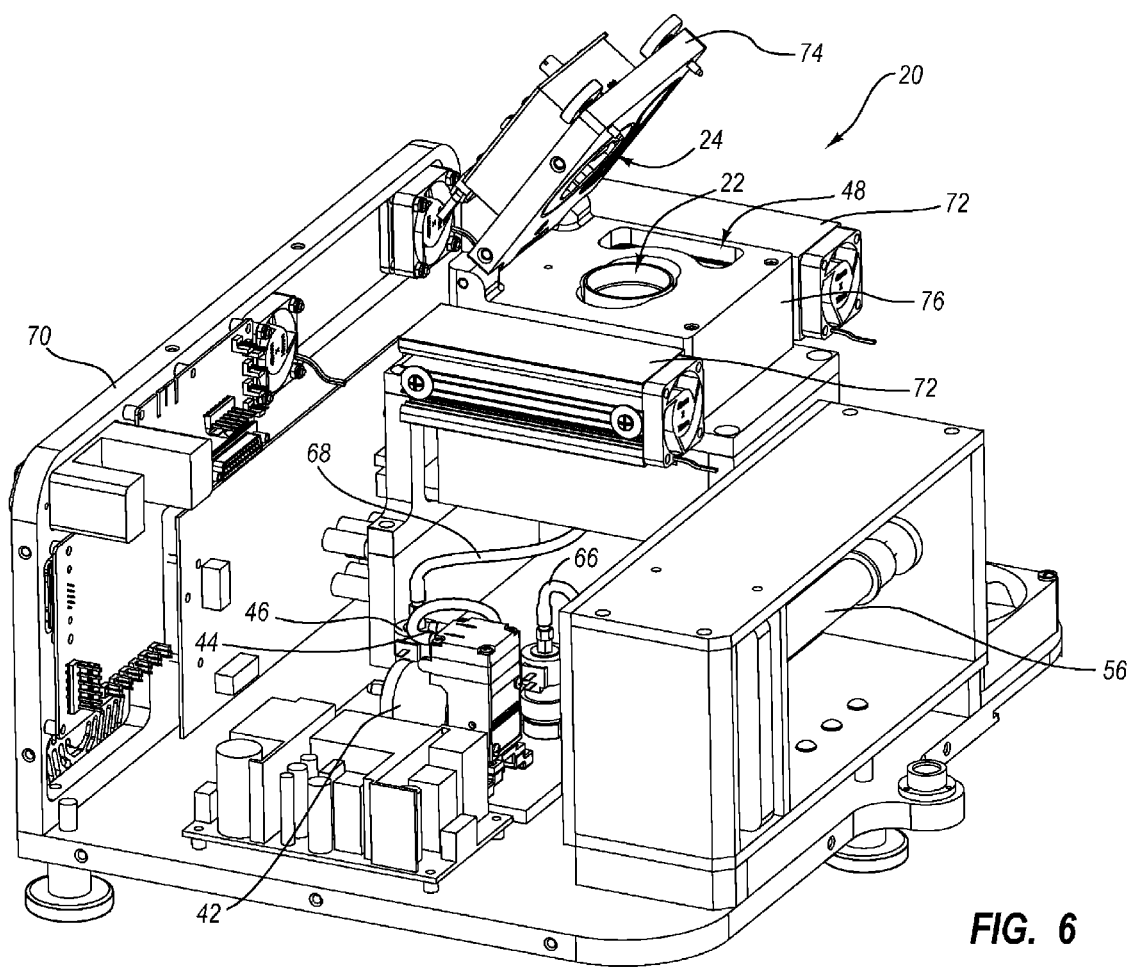
FIG. 6 is a perspective view of an exemplary measuring apparatus for measuring water activity and weight of a sample according to certain embodiments.

FIGS. 5 and 6 are perspective views showing additional embodiments of the invention. As illustrated in FIG. 5 and 6, a measuring apparatus 20 may include a moisture content adjustment device 30 (see, for example, FIG. 4) and a chamber 22. As detailed above, moisture content adjustment device 30 may include a pump 42, a pump inlet 44, a pump outlet 46, a moisture content adjustment valve 62, a humidification device 48, a humidification device inlet 66, a humidification device outlet 54, a desiccation device 56, desiccation device inlet 68, and desiccation device outlet 60. Pump 42 may include a diaphragm pump which may pump air received from pump inlet 44. Pump inlet 44 may be a nozzle on pump 42 which is open to an air supply external to pump 42. Pump outlet 46 may be a portion of tubing connected to pump 42 and valve 62.

Air pumped from pump outlet 46 to moisture content adjustment valve 62 may be directed to flow through humidification device inlet 66 to humidification device 48 or through desiccation device inlet 68 to desiccation device 56. Desiccation device inlet 68 may be a portion of tubing connected to valve 62 and to desiccation device 56. Desiccation device 68 may be a gas drying unit containing a desiccant material 58. Desiccant material 58 may comprise a visual indicator which may change color when the desiccant material 58 declines in desiccation activity. Desiccation device outlet 60 may be a portion of tubing connected to desiccation device 68 and chamber 22. Humidification device inlet 66 may be a portion of tubing connected to valve 62 and to humidification device 48. Humidification device 48 may include a water bath 50 which contains water. Humidification device inlet 66 may be connected to a lower portion of water bath 50 in humidification device 48. Humidification device 48 may produce a humidified gas mixture by receiving a gas mixture from pump outlet 46 and causing the gas mixture to increase in humidity as it passes from pump outlet 46 through the water in water bath 50, the gas mixture becoming substantially saturated with moisture as it passes through water bath 50. Humidification device outlet 54 may be a portion of tubing connected to humidification device 48 and chamber 22.

As illustrated in FIGS. 5 and 6, chamber 22 may be opened to receive a sample within chamber 22. Chamber 22 may additionally include a chamber outlet 34, which may allow any vapors introduced or produced in chamber 22 to be evacuated from the chamber (see, for example, FIG. 1). Chamber 22 may be formed in any shape, size, and configuration suitable for receiving and at least partially enclosing a food sample. According to some embodiments, the sample may be a soil sample, a pharmaceutical product, a consumer product, or any other suitable type of sample. In an exemplary embodiment, as shown in FIGS. 5 and 6, chamber 22 may comprise a chamber top portion 74 and a chamber bottom portion 76 which may be separated to introduce the sample into chamber 22. The chamber top portion 74 and chamber bottom portion 76 may be positioned to at least partially enclose the sample in chamber 22. In at least an additional embodiment, the chamber top portion 74 and chamber bottom portion 76 may be coupled by a hinge structure.

Chamber 22 may additionally include a sensor 24 which may be a chilled mirror dew point sensor (see, for example, FIG. 2). The sensor may measure the water activity of a sample in chamber 22. As illustrated in FIGS. 5 and 6, sensor 24 may be at least partially positioned inside chamber 22. Chamber 22 may also include a weighing device 26 which may be a magnetic force balance (see, for example, FIG. 1). Chamber 22 may additionally include a circulating device 41 which may be a fan (see, for example, FIG. 2). Chamber 22 and humidifier 30 may be positioned in the same thermal environments to keep them at similar temperatures.

As illustrated in FIG. 6, a housing 70 may at least partially enclose and protect measuring apparatus 20. Housing 70 may also help maintain substantially constant temperature within measuring apparatus 20, particularly chamber 22. As further illustrated in FIG. 6, measuring apparatus 20 may also include heating/cooling elements 72 coupled to chamber 22. Heating/cooling elements 72 may maintain chamber 22 at a substantially constant temperature. Heating/cooling elements 72 may be any device or combination of devices suitable for maintaining a substantially constant temperature in chamber 22. In at least an additional embodiment, heating/cooling elements 72 may be configured to contact and heat or cool a gas supplied by moisture content adjustment device 30 prior to the gas reaching chamber 22.

Figure 7:
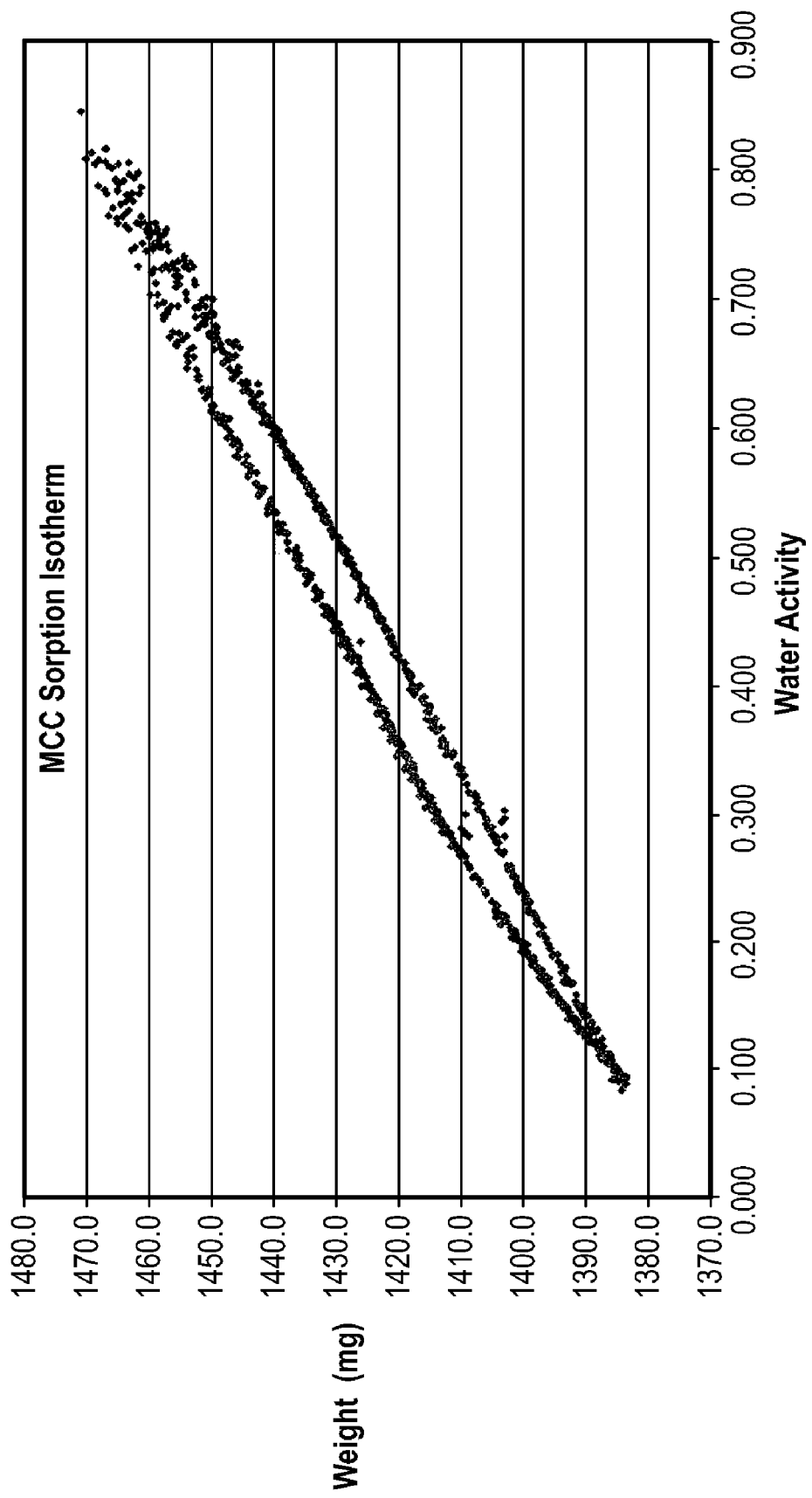
FIG. 7 is a graph of a moisture sorption isotherm generated using data obtained by an exemplary measuring apparatus for measuring water activity and weight of a sample.

FIG. 7 shows a moisture sorption isotherm graph generated from data obtained by at least one embodiment of a measuring apparatus 20. The data in FIG. 7 was obtained by measuring a sample of microcrystalline cellulose in measuring apparatus 20. The moisture content of the sample of microcrystalline cellulose was adjusted by measuring apparatus 20. In particular, moisture content was removed from chamber 22 of measuring apparatus 20 to obtain data used to generate a first portion of the moisture sorption isotherm graph shown in FIG. 7. Additionally, moisture content was added to chamber 22 of measuring apparatus 20 to obtain data to generate a second portion of the isotherm moisture sorption graph shown in FIG. 7. The graph in FIG. 7 shows the moisture sorption isotherm data points in terms of sample weight (in mg), and water activity.

The preceding description has been provided to enable others skilled in the art to best utilize the invention in various embodiments and aspects and with various modifications as are suited to the particular use contemplated. This exemplary description is not intended to be exhaustive or to limit the invention to any precise form disclosed. Many modifications and variations in the form and details are possible without departing from the spirit and scope of the invention. In addition, for ease of use, the words "including" and "having," as used in the specification and claims, are interchangeable with and have the same meaning as the word "comprising." It is intended that the scope of the invention be defined by the following claims.

What is claimed is:

1. A measurement apparatus comprising:
    a chamber;
    a sensor configured to measure water activity inside of a sample in the chamber;
    a moisture content adjustment device connected to the chamber and configured to change moisture content in the chamber.

2. The apparatus of claim 1, further comprising a weighing device coupled to the chamber.

3. The apparatus of claim 2, further comprising an isotherm generation module configured to receive measurements from the sensor device and the weighing device, the isotherm generation module being configured to generate an isotherm for a sample positioned in the chamber.

4. The apparatus of claim 3, wherein the isotherm generation module generates the isotherm by compiling a plurality of data points, each data point in the plurality of data points representing a measurement received from the sensor device and a measurement received from the weighing device.

5. The apparatus of claim 2, wherein the weighing device comprises at least one of:
    a scale coupled to the chamber;
    a balance coupled to the chamber.

6. The apparatus of claim 5, wherein the balance comprises a magnetic force balance.

7. The apparatus of claim 2, wherein at least a portion of the weighing device is positioned within the chamber.

8. The apparatus of claim 1, further comprising a fan positioned within the chamber.

9. The apparatus of claim 1, further comprising at least one of:
    a heating element coupled to the chamber;
    a cooling element coupled to the chamber.

10. The apparatus of claim 1, further comprising at least one of:
    a heating element configured to heat gas supplied by the moisture content adjustment device;
    a cooling element configured to cool gas supplied by the moisture content adjustment device.

11. The apparatus of claim 1, further comprising a valve configured to control passage of air between the chamber and a region external to the chamber.

12. The apparatus of claim 1, wherein the moisture content adjustment device comprises a humidification device.

13. The apparatus of claim 1, wherein the moisture content adjustment device comprises a desiccation device.

14. The apparatus of claim 1, wherein the moisture content adjustment device comprises:
    a gas supply;
    a pump configured to supply gas from the gas supply to the chamber.

15. The apparatus of claim 14, wherein the moisture content adjustment device further comprises:
    a humidification device;
    a desiccation device;
    a valve configured to deliver gas from the pump to at least one of:
        the humidification device;
        the desiccation device.

16. The apparatus of claim 1, wherein the sensor comprises at least one of:
    a water activity sensor;
    a humidity sensor;
    a dew point sensor; and
    an optical sensor.

17. The apparatus of claim 16, wherein the sensor comprises a chilled-mirror dew point sensor positioned within the chamber.

18. A method comprising:
    determining a first water activity measurement of a sample in a chamber during a first time period;
    determining a first weight of the sample in the chamber during the first time period;
    changing moisture content in the chamber during a second time period, the second time period being after the first time period;
    determining a second water activity measurement of the sample during a third time period, the third time period being after the second time period;
    determining a second weight of the sample during the third time period.

19. The method of claim 18, further comprising:
changing the moisture content in the chamber during a fourth time period, the fourth time period being after the third time period;
determining a third water activity measurement of the sample during a fifth time period, the fifth time period being after the fourth time period;
determining a third weight of the sample during the fifth time period.

20. The method of claim 18, further comprising preventing a change in moisture content in the chamber during at least one:
determining the first water activity measurement of the sample in the chamber during the first time period;
determining the first weight of the sample in the chamber during the first time period.

21. The method of claim 18, further comprising at least one of:
heating the chamber to within a specified temperature range;
cooling the chamber to within a specified temperature range.

22. The method of claim 18, further comprising:
circulating air within the chamber during at least one of:
determining the first water activity measurement of the sample in the chamber during the first time period;
determining the second water activity measurement of the sample in the chamber during the second time period.

23. The method of claim 18, wherein determining the first water activity measurement of the sample is performed at least substantially simultaneously with determining the first weight of the sample.

24. The method of claim 18, wherein determining the first water activity measurement is performed while the sample is positioned on a balance in the chamber.

25. The method of claim 18, wherein changing the moisture content in the chamber comprises at least one of:
adding moisture to the chamber;
removing moisture from the chamber.

26. The method of claim 25, wherein changing the moisture content in the chamber comprises supplying a gas and vapor mixture to the chamber.

27. A computer-implemented method for generating an isotherm, the computer-implemented method comprising:
determining a first water activity measurement of a sample during a first measuring period, the first water activity measurement being determined with a water activity sensor;
determining a first weight of the sample during the first measuring period, the sample being positioned in a chamber during the first measuring period;
determining a first isotherm data point based on the first water activity measurement of the sample and the first weight of the sample.

28. The computer-implemented method of claim 27, further comprising changing moisture content in the chamber after the first measuring period and before a second measuring period.

29. The method of claim 28, wherein changing the moisture content in the chamber comprises at least one of:
adding moisture to the chamber;
removing moisture from the chamber;
controlling a temperature of the chamber and sample.

30. The method of claim 27, further comprising:
adding moisture content to the chamber after the first measuring period and before a second measuring period;
removing moisture content from the chamber after the second measuring period and before a third measuring period.

31. The method of claim 27, wherein determining the first water activity measurement of the sample is performed at least substantially simultaneously with determining the first weight of the sample.

32. The method of claim 27, wherein determining the first water activity measurement is performed while the sample is positioned on a balance in the chamber.

33. The method of claim 27, further comprising:
determining a hydration curve of an isotherm based on a plurality of water activity measurements of the sample and a plurality of weights of the sample, wherein:
the plurality of water activity measurements comprises the first water activity measurement;
the plurality of weights comprises the first weight;
each water activity measurement in the plurality of water activity measurements is determined while the sample is in the chamber;
each weight in the plurality of weights is determined while the sample is in the chamber.

34. An isotherm generator comprising:
a chamber;
a sensor configured to measure water activity of a sample in the chamber;
a moisture content adjustment device connected to the chamber and configured to change moisture content in the chamber;
a weighing device coupled to the chamber and configured to weigh the sample in the chamber;
an isotherm generation module configured to receive water activity measurements from the sensor device and weight measurements from the weighing device, the isotherm generation module being configured to generate an isotherm for the sample, the isotherm being based on the water activity measurements and the weight measurements.

35. The isotherm generator of claim 34, wherein the weighing device comprises a magnetic force balance.

36. The isotherm generator of claim 34, wherein the sensor device comprises a chilled-mirror dew point sensor.

37. The isotherm generator of claim 34, wherein the sample comprises at least one of:
a food product;
a soil sample;
a pharmaceutical product;
a consumer product.

38. The isotherm generator of claim 34, further comprising:
a gas supply;
a pump configured to pump gas from the gas supply to the chamber.

39. The isotherm generator of claim 34, wherein the moisture content adjustment device further comprises:
a humidification device;
a desiccation device;
a valve configured to deliver gas from the pump to at least one of:
the humidification device;
the desiccation device.

40. The isotherm generator of claim 34, further comprising:
a heating device, the hearing device being configured to control a temperature of the chamber;
a cooling device, the cooling device being configured to control a temperature of the chamber.

* * * * *